United States Patent
Brown et al.

[11] Patent Number: 6,152,138
[45] Date of Patent: Nov. 28, 2000

[54] KINESIOLOGIC MOUTHPIECE AND METHOD

[76] Inventors: Thomas J. Brown, 1146 Guinevere; Thomas W. Brown, 1421 LaChateau, both of Liberty, Mo. 64068

[21] Appl. No.: 09/256,004

[22] Filed: Feb. 23, 1999

Related U.S. Application Data

[63] Continuation-in-part of application No. 08/695,390, Aug. 12, 1996, Pat. No. 5,873,365.
[51] Int. Cl.⁷ ..................................................... A61C 5/14
[52] U.S. Cl. ........................................... 128/859; 128/861
[58] Field of Search ................................... 128/846, 848, 128/859–862

[56] References Cited

U.S. PATENT DOCUMENTS

| | | | |
|---|---|---|---|
| 3,532,091 | 10/1970 | Lerman | 128/861 |
| 3,682,164 | 8/1972 | Miller | 128/861 |
| 4,063,552 | 12/1977 | Going | 128/859 |
| 5,339,832 | 8/1994 | Kittelsen | 128/862 |

*Primary Examiner*—Michael A. Brown
*Attorney, Agent, or Firm*—Shughart, Thomson, & Kilroy, P.C.

[57] ABSTRACT

A kinesiological mouthpiece includes a strap assembly with a bridge, a pair of extensions extending generally rearwardly and outwardly from the bridge and a pair of wings extending generally rearwardly from the extensions. The strap assembly is flexible for forming in a generally U-shaped use configuration. The wings are displaced at a different level from the bridge whereby the bridge can be positioned generally between the lower teeth and the lower lip with the wings approximately located on bite lines of the back teeth. A pair of bitepad assemblies are rotatably and longitudinally-adjustably mounted on the wings and each includes a bitepad with upper and lower contact surfaces for contacting by the back teeth. An occlusal support method includes the steps of providing a strap assembly, placing the strap assembly around the lower teeth, adjustably and rotatably mounting a pair of bitepad assemblies on the strap assembly, placing the bitepad assemblies between the back teeth and relieving tension on the temporomandibular joint.

7 Claims, 6 Drawing Sheets ent bitepad assembly includes a bitepad. The bitepads can be adjusted longitudinally and rotationally with respect to the wings to adjust their positions and are located between the users upper and lower rear teeth to provide occlusal support and to space the rear teeth sufficiently to prevent bruxism and teeth grinding. The rearward most edge of the bitepad is thicker than the forwardmost edge. An inward-outward adjustment assembly is provided for adjusting the positions of the bitepads relative to the wings in directions corresponding to inward and outward movements of the bitepads in a user's mouth. Various bitepad heights and shapes can be provided as necessary for a particular user to accommodate a user's dentition and TMJ alignment.

KINESIOLOGIC MOUTHPIECE AND METHOD

CROSS-REFERENCE TO RELATED APPLICATION

This application is a continuation-in-part of application Ser. No. 08/695,390, also entitled KINESIOLOGICAL MOUTHPIECE AND METHOD, filed Aug. 12, 1996 is now U.S. Pat. No. 5,873,365.

BACKGROUND OF THE INVENTION

1. Field of the Invention

The present invention generally relates to kinesiologic mouthpieces for occlusal support and in particular to a kinesiologic mouthpiece which provides spacing between the rear teeth to avoid bruxism (teeth clenching) and teeth grinding.

2. Description of the Related Art

Kinesiology is commonly applied to various activities, including sports, for optimizing the performance of the participants. For example, the proper alignment and orientation of the skeletal structure is considered a significant factor in optimizing athletic performance. Thus, athletic training for many sports emphasizes correct posture, positioning, stance, etc. for developing effective techniques.

Another factor common to many types of sports is the need for strength. Greater power and endurance, and the ability to apply same with proper techniques, are significant factors in determining the outcome of many athletic contests. Athletes therefore typically spend large amounts of time practicing their techniques and engaging in physical training to increase strength, speed, endurance, coordination, reflexes, etc.

A number of factors effect an athlete's ability. Factors such as genetic make-up are beyond the athlete's control. However, other performance-effecting factors, such as diet and conditioning, are within the athlete's control and receive considerable attention in athletic training programs.

Mandibular position and orientation of the temporomandibular joint ("TMJ") have been linked to muscular strength and athletic performance. For example, objective evidence of this correlation was reported in Smith, S. D. "Muscular Strength correlated to Jaw and the Temporomandibular Joint." N.Y State Dental Journal 44(7):279–82, 1978. Various problems associated with bruxism (teeth clenching), grinding and temporomandibular joint ("TMJ") misalignment have been reported, and include chronic headaches and other physiological problems. See, for example:

Gelb, H., and Tarte, J. A two year clinical dental evaluation of 200 cases of chronic headache: The crania cercicalmandibular syndrome. JADA 91:1230–1236, December 1975:

Gelb, H., and Berstein, I. Clinical evaluation of 200 patients with TMJ syndrome: J of Pros. Dent. 49(2) :234–243, February 1983.

A partial solution to TMJ syndrome and dysfunction has been achieved through the use of mandibular orthopedic repositioning appliances ("MORA"), and the benefits of such devices in athletics have been reported in the literature, such as:

Jakush, J. Divergent views: can dental therapy enhance athletic performance? JADA 104:292–298, March 1982.

Kaufman, R. S. Case reports of TMJ repositioning to improve scoliosis and the performance of athletes. N.Y. State Dent. J. 40(4):206–209, 280, April 1980.

Kaufman, A. and Kaufman, R. Usefulness of the MORA to reduce headaches on the U.S. Olympic Luge Team. Basal Facts. In Press.

Kaufman, A. and Kaufman, R. Effects of the Mora on members of a football team. Quintessense International 6:677–681, June 1983.

The effects of TMJ positioning on muscular strength were also reported in:

Williams, M. O.: Chaconis, S. J.: and Bader, P. The effects of mandibular position on appendage muscle strength. J. of Pros. Dent. 49(4):560–567, April 1983.

Mouth guards are commonly utilized in sports for protecting the head, neck and teeth, as discussed in:

Stenger, J., Lawson E., Wright, J.; and Rickets, J. Mouth guards: Protection against shock to head, neck and teeth. JADA 69:273, 1964.

In addition to providing protection against shock, TMJ positioning can be accomplished with mouthpieces, such as the MORA's described in the Geib, et al. article noted above.

The negative effects of teeth grinding and clenching include tension, stress, lack of concentration, fatigue, etc., all of which can adversely effect performance. In athletic contests it is particularly desirable to enhance performance and eliminate physical characteristics which could hamper same. In many athletic competitions relatively small advantages can control the outcome. For example, slight advantages in speed, strength and coordination can be sufficient to tip the balance in favor of a particular player or team. Conversely, if a player or a group of players on a team are suffering from stress, fatigue, lack of concentration, etc., the player or team will be likely to lose to an opponent which is free from such negative attributes.

Proper mandibular alignment is an important factor in enhancing performance through the elimination of teeth grinding and teeth clenching. Studies have concluded that sports performance can be enhanced by providing proper mandibular positioning and thus eliminating teeth grinding and clenching.

Mouthpieces are commonly used in a wide variety of sports and various styles have been devised to meet the requirements of particular sports. For example, mouthpieces which provide protection for the upper and lower lips and upper and lower sets of teeth are commonly used in contact sports. However, such mouthpieces have the disadvantage of interfering with speaking and breathing, and can be uncomfortable. Another disadvantage with this type of mouthpiece is that obtaining a proper fit for a particular player's mouth with standard sizes can be difficult. Thus, various sizes of mouthpieces must be provided in an attempt to accommodate as many individuals as possible, although such fitting procedures are generally somewhat of a compromise.

The present invention addresses these shortcomings of prior art mouthpieces by providing a kinesiological mouthpiece which can be adjusted for optimum fit.

SUMMARY OF THE INVENTION

In the practice of the present invention, a kinesiological mouthpiece is provided which includes a strap assembly having a bridge, a pair of extensions extending rearwardly, outwardly and upwardly therefrom and a pair of wings extending generally rearwardly from the extensions. The strap assembly is designed to fit over the lower teeth with the strap assembly located generally between the lower teeth and the lips. A pair of bitepad assemblies are rotatably and longitudinally adjustably mounted on the wings and each includes a bitepad for location between the upper and lower back teeth. An occlusal support method is provided which includes the steps of providing a strap assembly; placing the strap assembly around the lower teeth: adjustably and rotatably mounting a pair of bitepad assemblies on the strap assembly; placing the bitepad between the lower teeth; and relieving tension on a temporomandibular joint.

OBJECTS AND ADVANTAGES OF THE INVENTION

The principle objects and advantages of the present invention include: providing a kinesiological mouthpiece; providing such a mouthpiece which facilitates proper mandibular closure; providing such a mouthpiece which facilitates proper alignment and positioning of the temporomandibular joint; providing such a mouthpiece which prevents teeth grinding and clenching; providing such a mouthpiece which provides a fissure between the upper and lower teeth; providing such a mouthpiece which can facilitate an increase in sports performance; providing such a mouthpiece which reduces the effects of teeth clenching and grinding in athletes; providing such a mouthpiece which can enhance physical performance; providing such a mouthpiece which can enhance concentration; providing such a mouthpiece which is adjustable in fit to accommodate its wearers; providing such a mouthpiece which is economical to manufacture, efficient in operation, capable of a long operating life and particularly well adapted for the proposed usage thereof; providing such a mouthpiece which is relatively comfortable; providing such a mouthpiece which is relatively concealed in use; providing such a mouthpiece which avoids substantial interference with breathing and speaking; and providing such a mouthpiece which is usable by a wide range of athletes and others.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

I. Introduction and Environment

Figure 1:
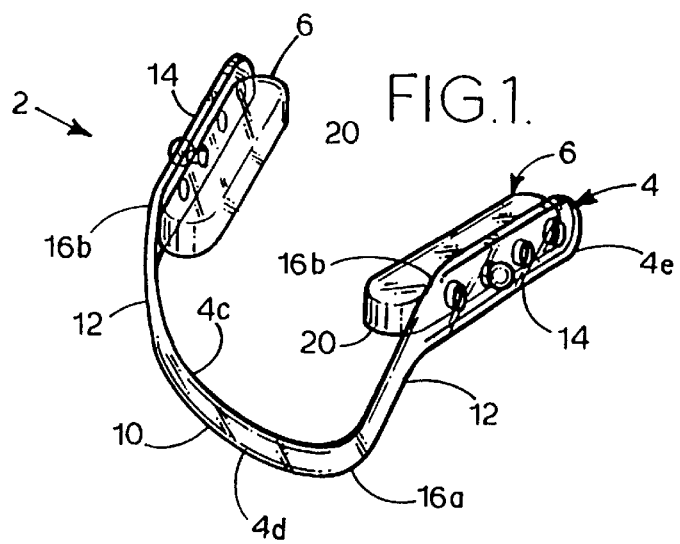
FIG. 1 is an upper, front, left side perspective view of a kinesiologic mouthpiece embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly" "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

Referring to the drawings in more detail, the reference numeral 2 generally designates a kinesiological mouthpiece embodying the present invention. The mouthpiece 2 generally comprises a strap assembly 4 which is positioned, for example, between the lower teeth and lip and a pair of bitepad assemblies 6, each of which is mounted on the strap and placed between the upper and lower molars on a respective side of the mouth. As will be explained in more detail hereinafter, the mouthpiece 2 provides occlusal support with a slight gap between the back teeth.

II. Strap Assembly 4

The strap assembly 4, as shown in FIGS. 1–4, includes first and second faces 4a,b (FIG. 3); rounded upper and lower edges 4c,d; and rounded corners 4e. The strap assembly further includes a bridge 10 (best seen in FIG. 4) with opposite sides 10a,b; a pair of extensions 12 each having a front end 12a connected to a respective bridge side 10a,b and a back end 12b; and a pair of wings 14 each including a front end 14a connected to a respective extension back end 12b and a free back end 14b. In a flat configuration as manufactured (again referring to FIG. 4), the bridge 10 is generally parallel to the wings 14 but offset therefrom, with the extensions 12 forming front and back obtuse-angled connections 16a,b at their respective connections to the bridge 10 and the wings 14.

Each wing 14 includes a plurality (e.g., four as shown in FIGS. 1–4) of receivers 18 positioned in longitudinally-spaced relation along a receiver line 18a (FIG. 4) which extends generally parallel to the upper and lower edges 4c,d at the wings 14. The receivers 18 extend between and are open at the strap faces 4a,b. The strap 4 preferably has rounded corners, edges, etc. for comfort, for example, along the edges 4c,d and at the wing back ends 14b which form corners 4e.

III. Bitepad Assemblies 6

Each bitepad assembly 6 (as shown in FIGS. 5–8) includes a bitepad 20 with first and second contact surfaces 20a,b; front and back rounded ends 20c,d; and inner and outer edges 20e,f. Each bitepad also includes a pin subassembly 22 comprising a shank 22a extending outwardly from a respective bitepad outer edge 20f and a ball 22b mounted on the outer end of each pin shank in spaced relation from a respective bitepad outer edge 20f. As with the strap assembly 4, the bitepad assemblies 6 preferably have rounded ends 20c,d and edges 20e,f for comfort.

Figure 8:
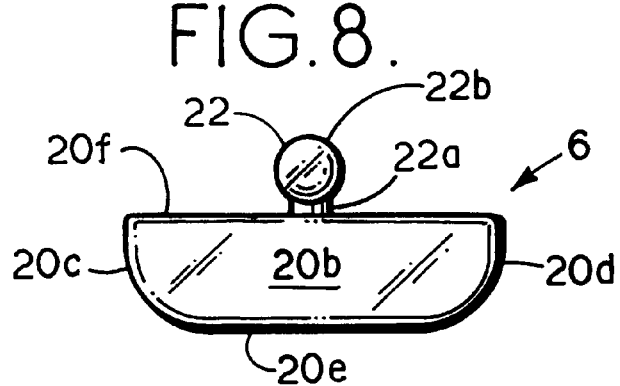
FIG. 8 is a top plan view of the bitepad assembly.
Figure 8A:
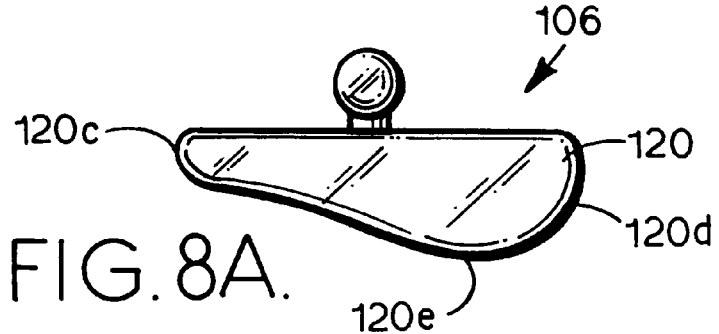
FIG. 8A is a plan view of a modified bitepad assembly.

FIG. 8A shows a modified form of a bitepad assembly 106 including a bitepad 120 with a modified configuration having a relatively narrow front end 120c, a relatively wide back end 120d and an inner edge 120e tapering therebetween. The modified bitepad assembly 106 provides an enlarged area at the bitepad back end 120d to provide greater contact area for the back teeth with the tapered inner edge thereof to facilitate ease of placement and retention in position. Such modified bitepad assemblies 106 can be used interchangeably with the bitepads 6.

Still further, the strap assembly 4 and the bitepad 6 can be formed integrally by molding or casting the mouthpiece 2 as a single article (not shown).

IV. Mouthpiece 2 Construction and Occlusal Support Method

The components of the mouthpiece 2 are preferably fabricated from a resilient, polymeric material from which the strap assembly 4 and the bitepad assemblies 6 can be stamped or otherwise formed. However, other manufacturing processes such as injection molding, vacuum forming, etc., can be utilized. The material chosen for the mouthpiece 2 is preferably washable for purposes of cleaning same.

The material comprising the strap assembly 4 is preferably chosen to provide sufficient flexibility to accommodate the shape of a person's dental structure, and may include a certain amount of memory to maintain such a shape. For example, ethylene vinyl acetate (EVA) has been found to be a suitable material. However, other materials with the desired characteristics of resiliency, flexibility and durability may be utilized. Moreover, the hardness of the materials can be controlled to provide desired performance characteristics.

The strap assembly 4 and the bitepad assemblies 6 are preferably formed separately to facilitate manufacturing, adjustability and to minimize cost of manufacture. However, the strap and bitepad assemblies 4, 6 can be integrally formed. Moreover, the displacement of the bridge 10 from the wings 14 can be varied to accommodate various wearers of the mouthpiece 2.

The adjustable mounting feature of the bitepad assemblies 6 enables the mouthpiece 2 to accommodate various wearers of various dental structures. The appropriate receiver 18 is chosen to accommodate a pin subassembly 22 of each bitepad assembly 6. Thus, the outermost/rearmost receivers are preferably utilized by wearers with larger bites, whereas receivers 18 which are more closely/forwardly spaced are preferably utilized for wearers with smaller dental bites.

Figure 2:
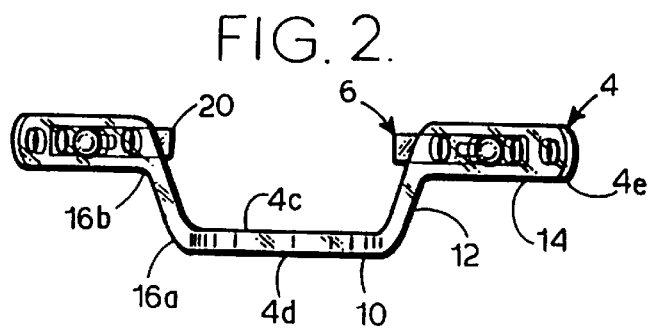
FIG. 2 is a front elevation view thereof.
Figure 3:
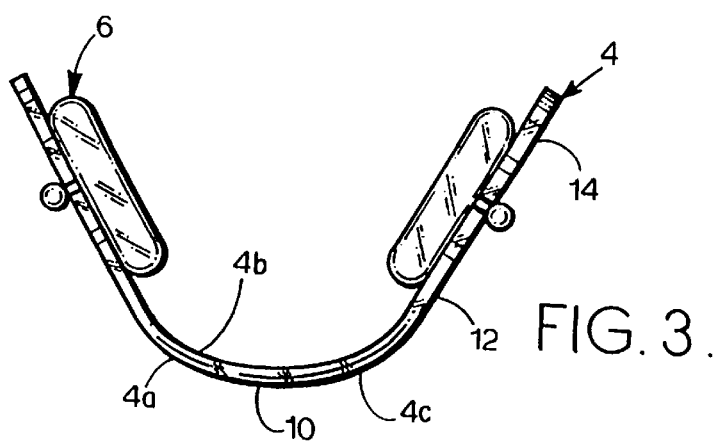
FIG. 3 is top plan view thereof.
Figure 4:
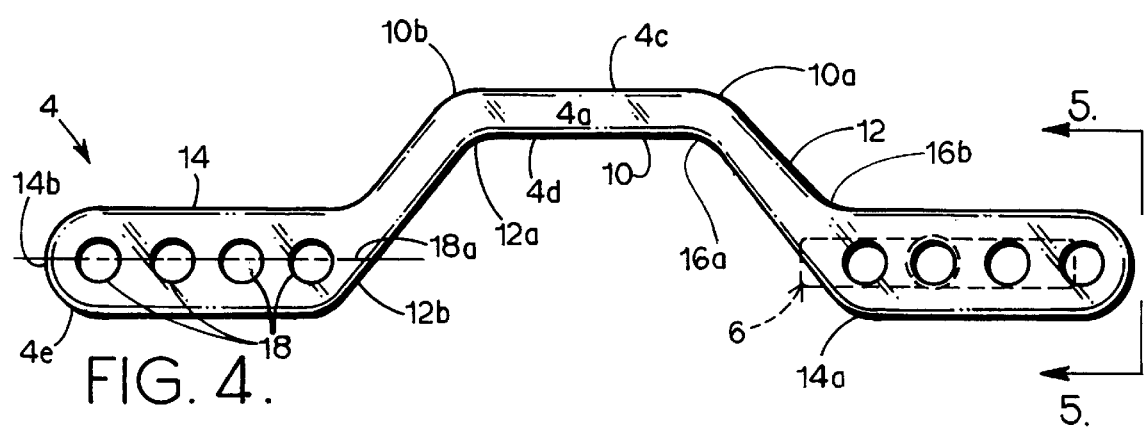
FIG. 4 is a front elevational view of a strap assembly thereof, shown in a flattened position, with a bitepad assembly thereof shown in dashed lines.
Figures 5, 6:
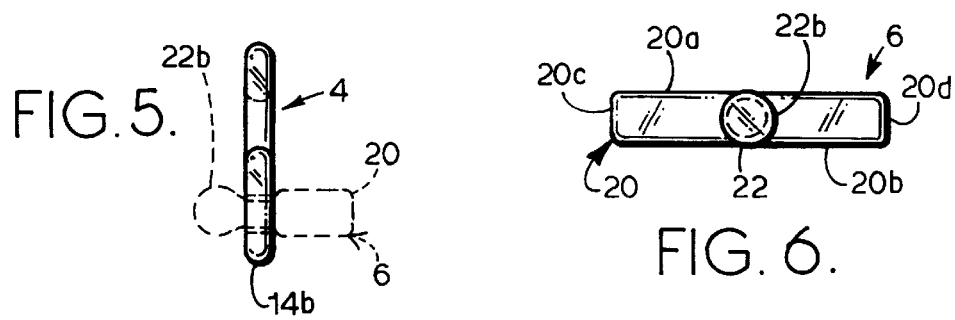
FIG. 5 is an end elevational view of the strap assembly, with the bitepad assembly shown in dashed lines.
FIG. 6 is a side elevational view of the bitepad assembly.
Figure 7:
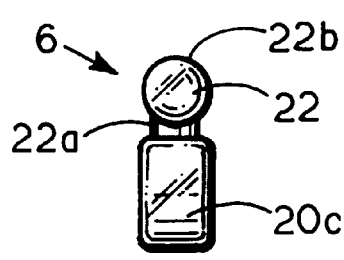
FIG. 7 is an end elevational view of the bitepad assembly.

As shown in FIGS. 1–3, the bitepad assemblies 6 are mounted on the wings 14 by passing the balls 22b through respective receivers 18 whereby the shanks 22a are securely and rotatably retained within the receivers 18. The mouthpiece is placed in the mouth with the strap assembly 4 primarily encircling the front/outside portions of the jaw and lower teeth and with the strap inner face 4b placed against the lower teeth. The angular orientation of the bridge-to-extension and the extension-to-wing connections or joints 16a,b places the wings 14 at a level of the person's bite.

Figure 9:
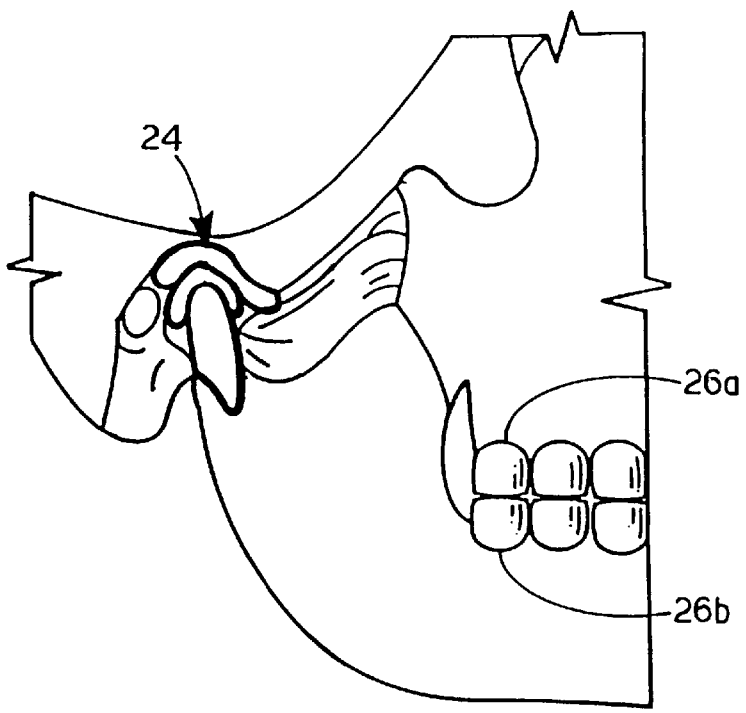
FIG. 9 is a side elevational view of a temporomandibular joint, shown with the teeth clenched.
Figure 10:
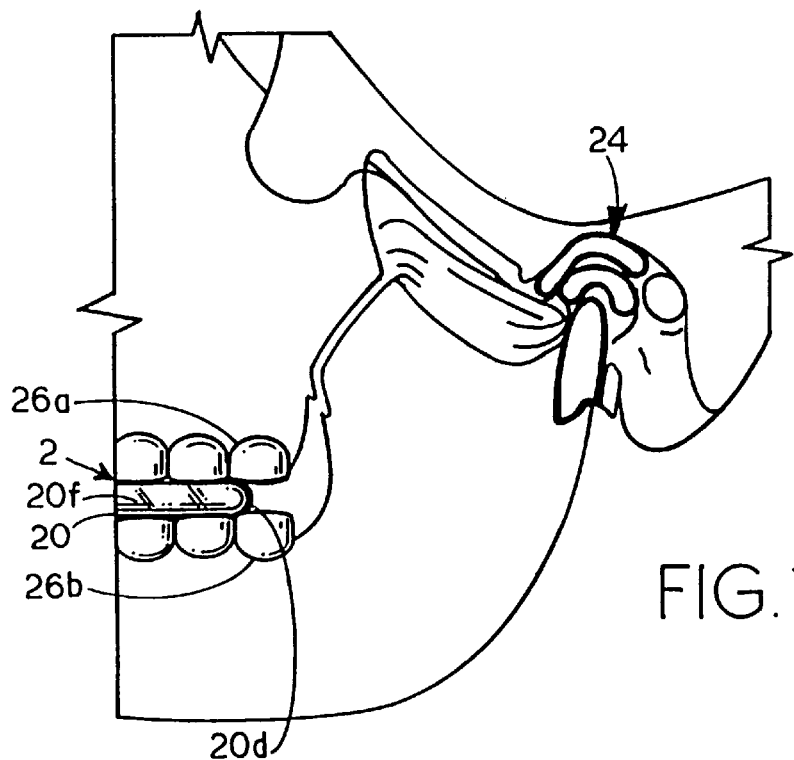
FIG. 10 is a side elevational view of the temporomandibular joint, shown with the teeth spaced by a mouthpiece embodying the present invention.

FIG. 9 shows the condition of the temporomandibular joint 24 of a person clenching their upper teeth 26a and lower teeth 26b together. As shown in FIG. 10, the bitepads 20 function to maintain a predetermined spacing of the back teeth 26a,b, and reposition the temporomandibular joint 24 to provide both optimum bite control and a tension-free joint while minimizing interference with other activities of the wearer, such as participation in physical sports, etc. By eliminating the problems associated with bruxism, teeth grinding and teeth clenching, improved performance can be obtained in a variety of physical endeavors, such as sports, etc.

The configuration of the strap assembly 4 (FIG. 1) with its bridge and wings spaced with respect to each other minimizes interference from wearing the mouthpiece 2 which might otherwise interfere with talking, eating, breathing, etc. It will be appreciated that the mouthpiece 2 can be easily and quickly placed in position, removed and disassembled for cleaning. Moreover, the rotational connection of the bitepad assembly 6 to the wings 14 permits the strap assembly 4, and particularly the bridge 10, to be raised or lowered as desired for comfort and optimum performance. Due to the relatively compact configuration of the strap assembly 4, the mouthpiece 2 is barely noticeable to either a wearer or to others. By fabricating it of a relatively clear or translucent material, the mouthpiece 2 can be relatively effectively concealed. Moreover, since it is generally positioned on the lower teeth behind the lower lips, breathing is generally not impaired and an athlete can breath substantially as heavily as normal with the mouthpiece 2 in place.

The mouthpiece 2 can be customized. For example, excess length of the strap assembly 4 can be removed by cutting off the ends of the wings 14. Also, with suitable resins or other fabricating material, the strap assembly 4 could be heated and stretched.

The mouthpiece 2 can be easily disassembled for cleaning, storage, etc. Also, the mouthpiece 2 can be shipped and packaged in a disassembled condition to minimize the space required by same. The components of the mouthpiece 2 are generally reversible, i.e., the strap assembly 4 could be flipped over, as could the bitepad assemblies 6.

V. First Modified Embodiment Kinesiologic Mouthpiece 202

Figure 11:
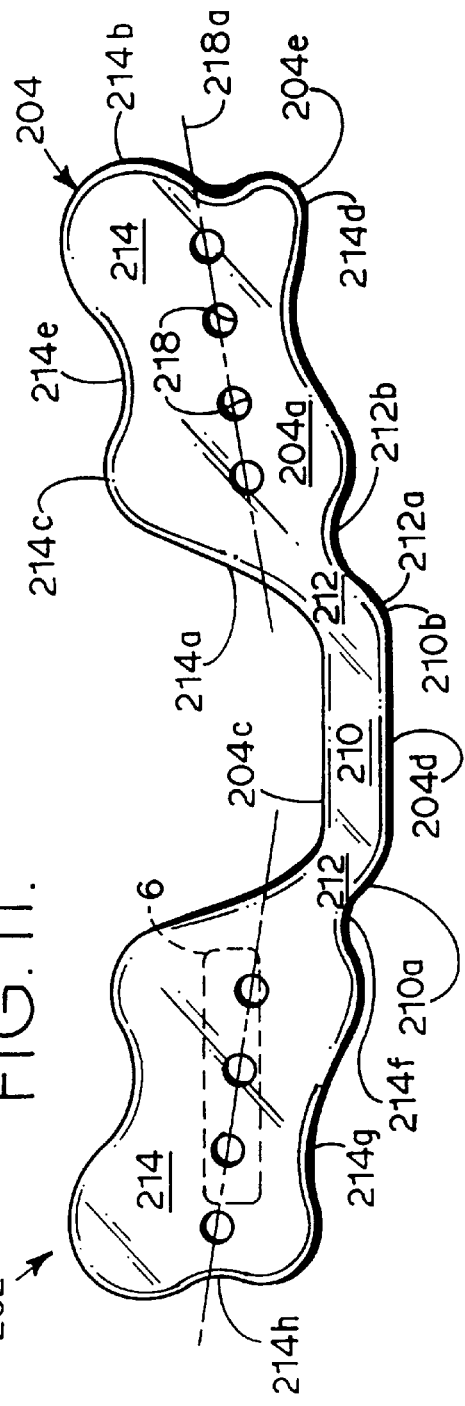
FIG. 11 is a front elevation of a strap assembly of a kinesiologic mouthpiece comprising a first modified embodiment of the present invention.

FIG. 11 shows a strap assembly 204 for a kinesiologic mouthpiece 202 comprising a modified embodiment of the present invention. The strap assembly 204 includes a first face 204a; a second face (not shown); upper and lower edges 204c,d and rounded corners 204e. The strap assembly 204 includes a bridge 210 with opposite sides 210a,b. A pair of extensions 212 each includes a front end 212a connected to a respective bridge side 210a,b and a back end 212b.

The strap assembly 204 includes a pair of wings 214 which are modified from the wings 14 described above. Each wing 214 includes a front end 214a connected to a respective extension back end 212b and a back end 214b. Each wing 214 also includes upper and lower edges 214c,d. Each wing upper edge 214c includes an upper recess 214e. Each wing lower edge 214d includes a lower front recess 214f located generally where the back end 212b of a respective extension 212 adjoins the front end 214a of a respective wing 214. Each wing lower edge 214d also includes a lower back recess 214g and each wing back end 214b includes a back end recess 214h. The recesses 214e–h all form gradual curves where they merge with respective wing edges 214c,d and wing back ends 214b.

Each wing 214 includes a plurality of receivers 218 (e.g. 4 are shown) which form a receiver line 218a. The receiver line 218a slopes downwardly from back-to-front whereby the frontmost receivers 218 are positioned at the lowest level, with each successive receiver 218 rearwardly being positioned at a slightly higher level than the proceeding one.

In operation, the greater overall heights of the wings 214 facilitate the proper positioning of the mouthpiece 202 and its retention in place. In particular, the greater heights of the wings 214 facilitate opening and closing the mouth while maintaining proper contact with the teeth and gums for retaining the mouthpiece 202 generally in a proper position. The strap assembly 204 can be provided with either bitepad assemblies 6 or bitepad assemblies 106 as described above, which can be attached in the same manner as described above. When the teeth are closed on the bitepads 6, the recesses 214e–h accommodate protrusions of the gums to provide a relatively comfortable fit. The downward slopes of the receiver line 218a function to adjust the overall proportions of the mouthpiece 202 for fit purposes whereby individuals with different sizes of mouths can be properly fitted by adjustably repositioning the bitepads 6. For example, with the bitepads 6 located in the frontmost receivers 218, a relatively small mouth could be accommodated, in which case it would probably be desirable to lower the positions of the bitepads 6 with respect to the bridge 10, which is accomplished automatically since the forwardmost receivers 218 are at the lowest receiver level.

VI. Second Modified Embodiment Kinesiologic Mouthpiece 302

Figure 12:
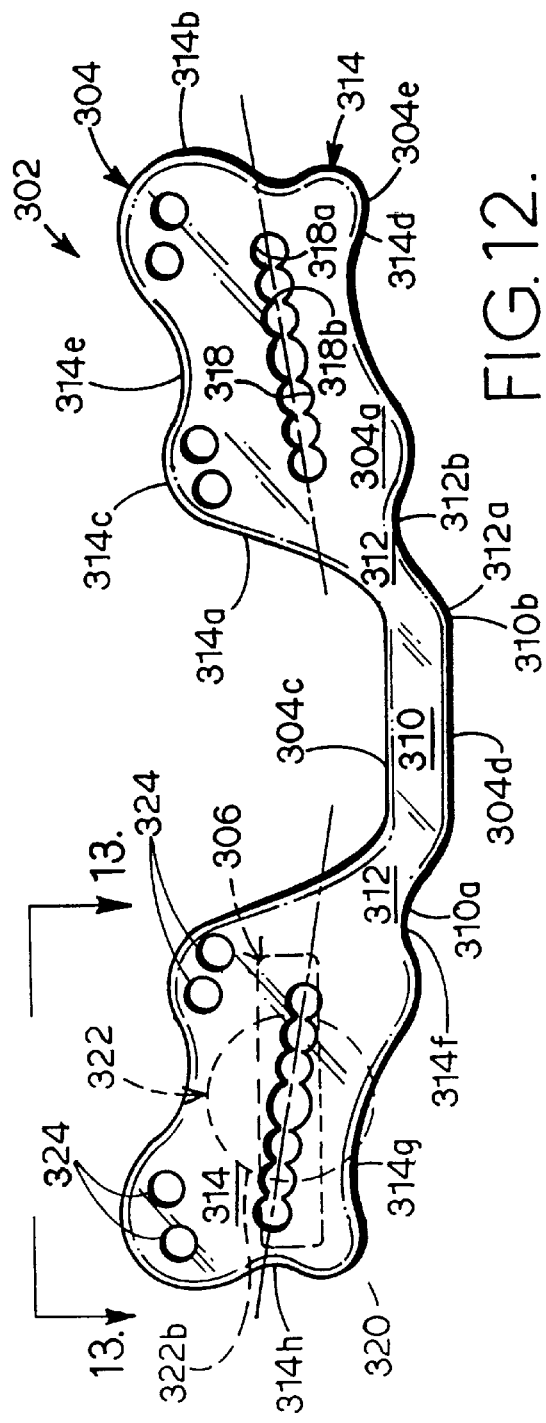
FIG. 12 is a front elevational view of a kinesiologic mouthpiece comprising a second modified embodiment of the present invention.
Figure 13:
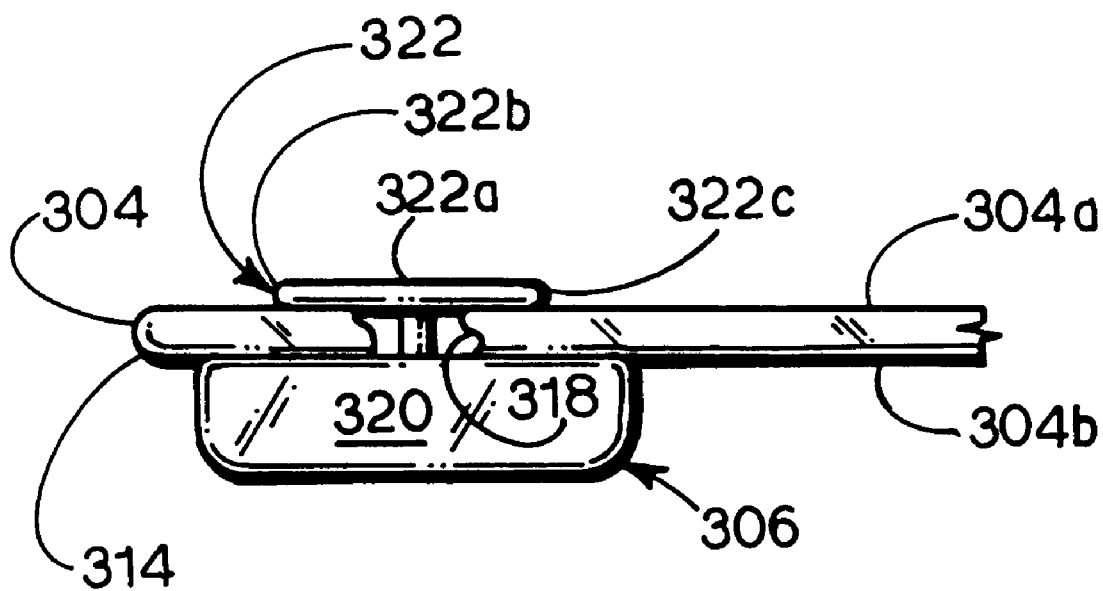
FIG. 13 is an enlarged, fragmentary, top plan view of the mouthpiece particularly showing a bitepad assembly thereof.
Figure 4:
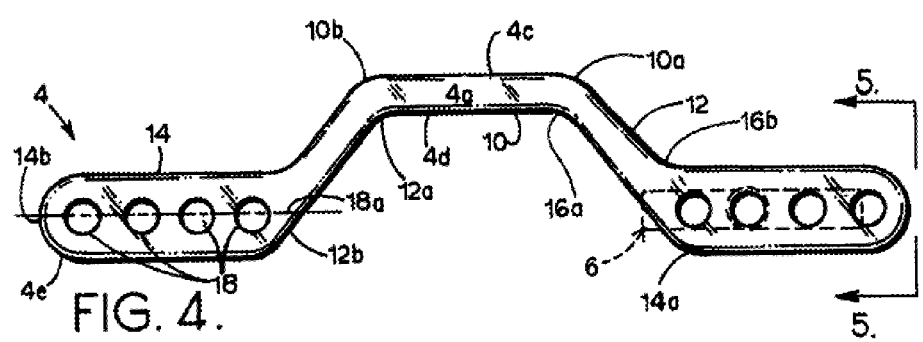
Figure 5:
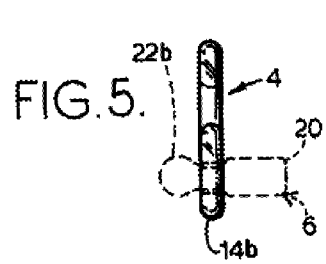
Figure 6:
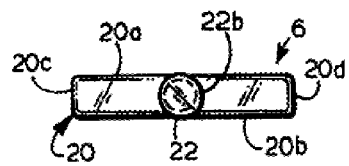
Figure 7:
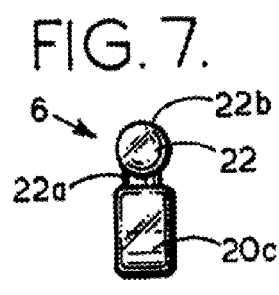
Figure 8:
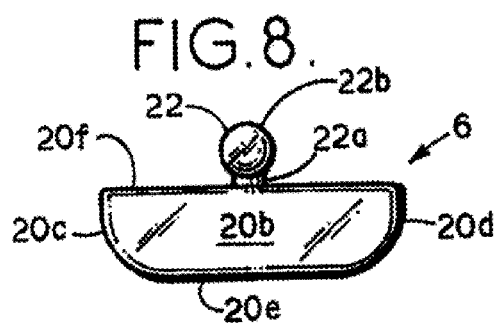
Figure 8A:
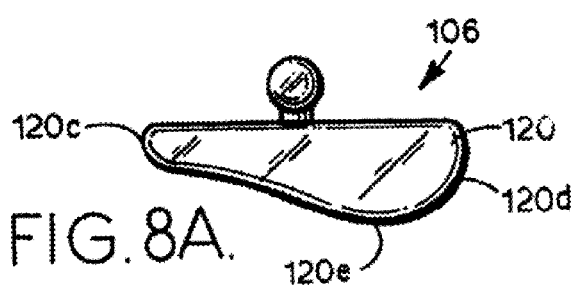
Figure 9:
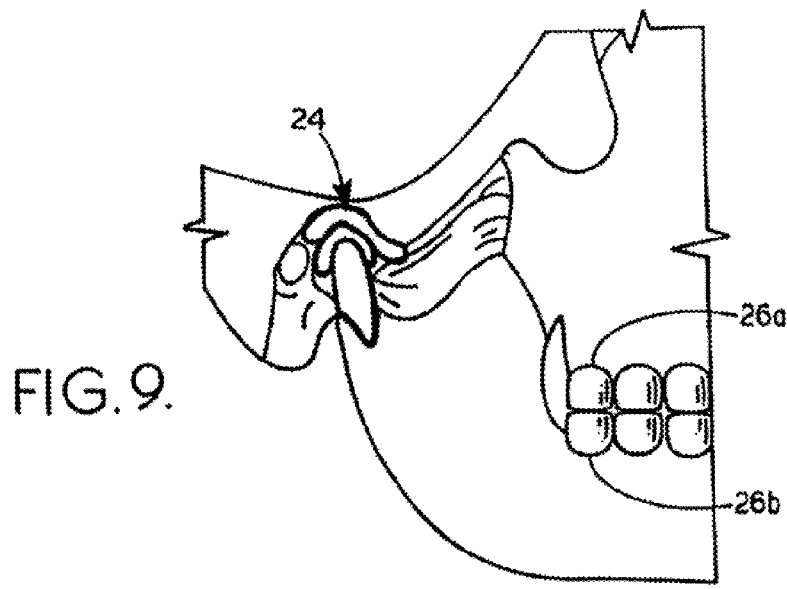
Figure 10:
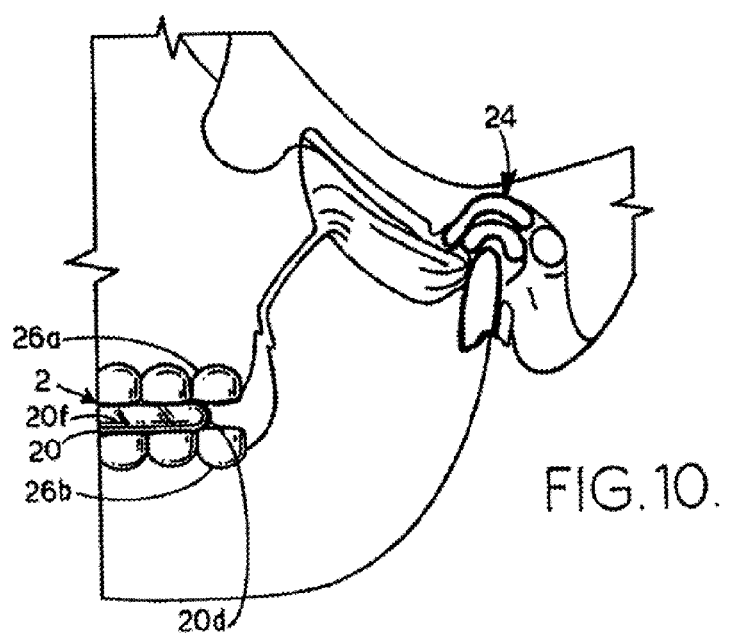
Figure 13:
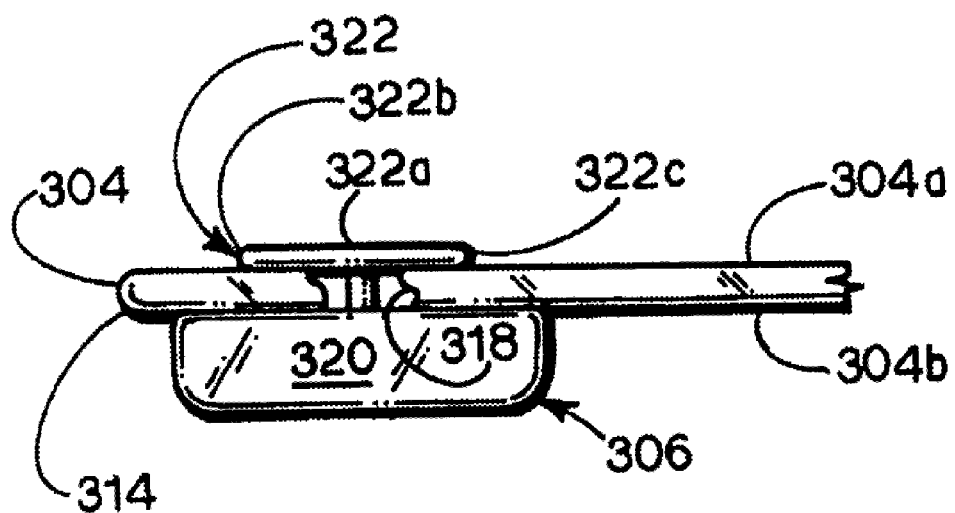

FIGS. 12–13 show a kinesiologic mouthpiece 302 comprising a second modified embodiment of the present invention and including a strap assembly 304 mounting a pair of bitepad assemblies 306.

The strap assembly 304 includes a first face 304a; a second face 304b; upper and lower edges 304c,d and rounded corners 304e. Strap assembly 304 includes a bridge 310 with opposite sides 310a,b. A pair of extensions 312 each includes a front end 312a connected to a respective bridge side 310a,b and a back end 312b.

The strap assembly 304 includes a pair of wings 314 which are modified from the wings 14 and 214 described above. Each wing 314 includes a front end 314a connected to a respective extension back end 312b and a back end 314b. Each wing 314 also includes upper and lower edges 314c,d. Each wing upper edge 314c includes an upper recess 314e and each wing lower edge 314d includes a lower front recess 314f and a lower back recess 314g. Each wing back end 314b includes a back end recess 314h. A multi-position, multi-receiver slot 318 is formed in each wing 314 and comprises a series of interconnected receivers 318a with connecting passages 318b therebetween. Each bitepad assembly 306 includes a bitepad 320 with a pin subassembly 322 comprising a shank 322a extending outwardly therefrom and mounting a flange 322b, which preferably is relatively thin and includes a rounded perimeter 322c. The relatively flat pin subassembly flange 322b provides user comfort since it protrudes only a short distance from the strap assembly first face 304a.

The second modified kinesiologic mouthpiece 302 is formed by inserting the flange 322b through the multi-position receiver slot 318 to a position where the wings 314 are captured between respective bitepads 320 and pin subassembly flanges 322b with pin subassembly shanks 322a extending through respective receiver slots 318. The passages 318b between the receivers 318a permit slidably repositioning the bitepad assemblies 306 on the wings 314. The bitepad assemblies 306 can thus be slid forward and back with their respective pin subassembly shanks 322a registering in respective receivers 318a. The multi-position, multi-receiver slots 318 thus provide a number of positions for the bitepad assembly 306 and facilitates relatively easy adjustment since the adjustments can be made without separating the bitepad assemblies 306 from the strap assembly 304.

Each wing 314 also includes a plurality of relief holes 324 which can be positioned, for example, in proximity to the wing upper edges 314c near the front and back ends 314f,g thereof. The relief holes 324 facilitate passage of saliva through the wings 314, and also increase the flexibility of the wings 314 in those areas.

The second modified embodiment kinesiologic mouthpiece 302 functions in a manner similar to the mouthpieces 2 and 202 described above, except that the positions of the bitepad assembly 306 can be adjusted without separating them from the strap assembly wings 314. Moreover, assembly can be simplified because the pin subassembly flanges 322b can be inserted through the multi-position receiver slots 318. The second modified embodiment kinesiologic mouthpiece 302 can thus be relatively easy to use, even for a person with reduced hand and finger capabilities, which can be associated with arthritis and other medical conditions.

VII. Third Modified Embodiment Kinesiologic Mouthpiece 402

A third modified embodiment of the present invention comprises a kinesiologic mouthpiece 402 (not shown) including the strap assembly 304 (FIG. 12) mounting a pair of bitepad assemblies 406 shown in FIGS. 14–17.

Figure 14:
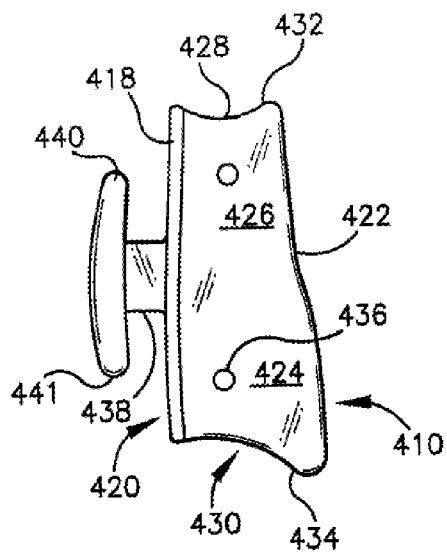
FIG. 14 is a top plan view of an inner core of a kinesioligic mouthpiece comprising a third modified embodiment of the present invention.
Figure 15:
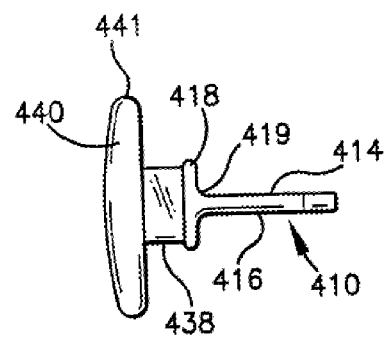
FIG. 15 is a front elevational view of the inner core.

Each bitepad assembly 406 includes a bitepad 408 comprising a hard inner core 410 and a relatively soft outer or encapsulating core 412. The inner core 410 provides greater durability than would otherwise exist. As shown in FIGS. 14 and 15 (which depict the bitepad 408 with the outer core 412 removed), the inner core 410 is generally cross-sectionally T-shaped and includes a top or upper surface 414, a bottom or lower surfaces 416, and a side surface or span 418, which is normal to the top and bottom surfaces, 414, 416. The interfaces 419 between the top and bottom surfaces 414, 416 and the span 418 are preferably rounded for maximum strength. The span 418 tapers inward along a distal end 420 to follow the natural shape of the bite pattern of most wearers. An inner edge 422 of the inner core 408 slopes from front to rear such that a rear or distal surface 424 of the inner core 410 is wider than a front or proximate surface 426 of the inner core 410. A front recess 428 and a rear recess 430 are formed in respective front and rear edges 432, 434 of the inner core 410. A plurality (in the present embodiment, two) of holes or openings 436 are formed in the inner core 410, the function of which will be discussed in greater detail below.

A cylindrical shaft 438 extends outward or away from the span 418 and mounts a flange 440 with a rounded perimeter 441. The flange can be used in conjunction with the strap assembly 304 to mount the bitepad assemblies 406 thereto. The function and operation of the flange 440 is identical to that of the flange 322b of the bitepad assembly 306 used in conjunction with the strap assembly 304 as previously described.

Figure 16:
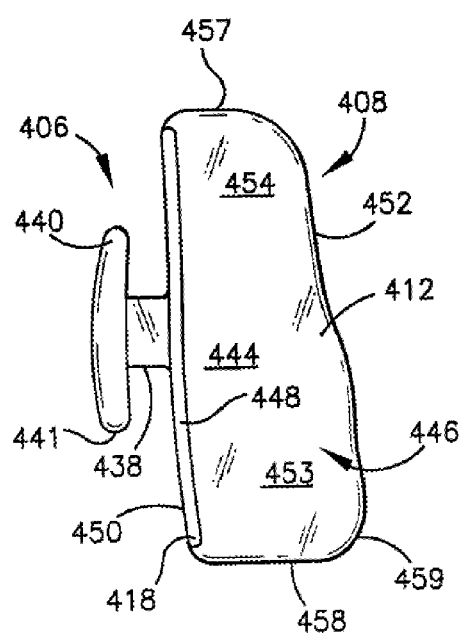
FIG. 16 is a top plan view of a bitepad assembly of the mouthpiece comprising the third modified embodiment.
Figure 17:
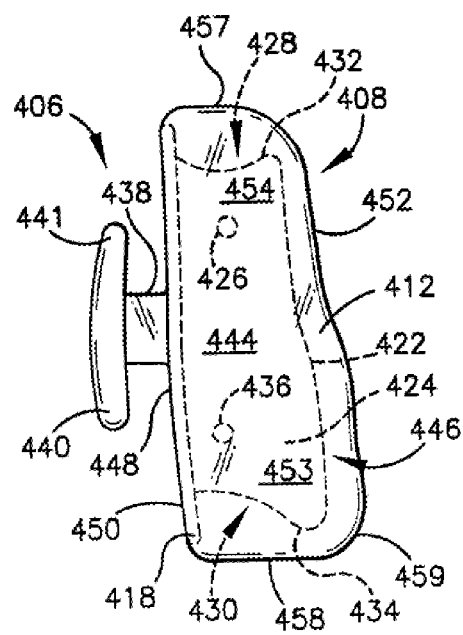
FIG. 17 is a top plan view of the bitepad assembly of the third modified embodiment showing both an outer core and the inner core.

The outer core 412, as shown in FIGS. 16 and 17, includes a top or upper surface 444 and a bottom or lower surface 446 and is formed by injecting a suitable amount of a material such as kraton or polypropylene onto and covering the top and bottom surfaces 414, 416 and the span 418 of the inner core 410. Increased adhesion of the outer core 412 to the inner core 410 occurs during injection around the openings 436 of the inner core 410. The upper 444 and lower 446 surfaces serve as contact surfaces for the wearer's teeth. The outer core 412 is generally formed to follow the shape of the inner core 410 such that an outer edge 448 of the outer core 412 abuts the span 418 and tapers inward along a distal portion 450 of said edge 448. An inner edge 452 of the outer core slopes from front to rear such that a rear or distal surface 453 of the outer core 412 is wider than a front or proximate surface 454 of the outer core 412. The inner 452 and outer 448 edges connect a rounded front edge 457 and a straight rear edge 458 of the outer core 412. Corners 459 of the outer core 412 are rounded for comfort of the wearer. The outer core 412 thickness increases uniformly from a relatively thin distal portion thickness 460 (not shown) to a relatively thick front portion thickness 462 (not shown) to follow the bite pattern of most wearers. The front edge thickness 462 is approximately equal to but slightly less than the height of the span 418. Referring to FIG. 16, the upper 444 and lower 446 surfaces are formed to follow the bite patten of most wearers by following the Curve of Wilson upwardly and downwardly along and the Curve of Spee rightwardly and leftwardly along the surfaces 444, 446.

VIII. Fourth Modified Embodiment Kinesiologic Mouthpiece 502

Figure 18:
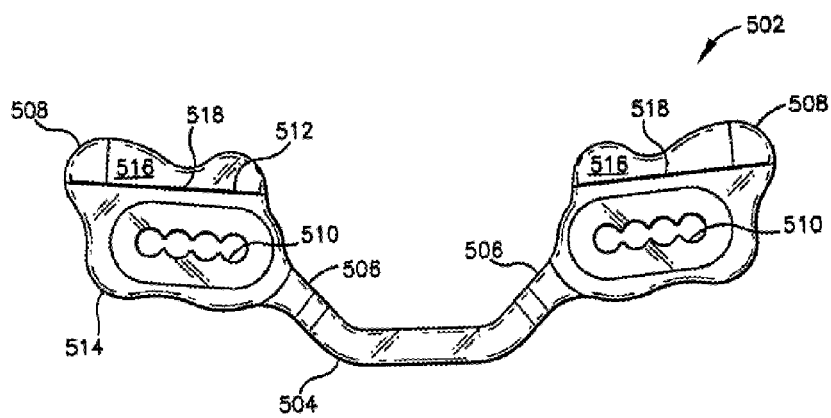
FIG. 18 is a front elevational view of a strap assembly for a fourth modified embodiment of the present invention.

FIG. 18 shows a further modified strap assembly 502 for a kinesiologic mouthpiece comprising a fourth modified embodiment of the present invention. The strap assembly 502 includes a bridge 504 which is dimensionally wider and thinner than the previously described embodiments for greater comfort. The bridge 504 is connected to a pair of extensions 506 with similar wider and thinner dimensions. A pair of wings 508 are mounted on the extensions 506 and project outwardly therefrom.

Each wing includes a plurality (e.g. four are shown) of holes 510 which are serially interconnected and allow adjustable repositioning of a respective bitepad assembly. Without limitation on the number of holes 510 which could be employed with the present invention, the configuration shown with four holes has been found to provide sufficient adjustability for most applications.

Each wing 508 also includes a channel 512 in which a bitepad assembly flange (i.e. 322b or 440 described above) can adjustably slide. Each wing 508 further includes a wing body 514 and a wing flap 516 separated by a wing relief groove 518 which functions as a hinge to provide flexibility between the wing body and flap 514, 518. The strap assembly 502 is adapted for use with bitepad assemblies such as 306 and 406 described above.

It is to be understood that while certain forms of the present invention have been illustrated and described herein, it is not to be limited to the specific forms or arrangement of parts described and shown.

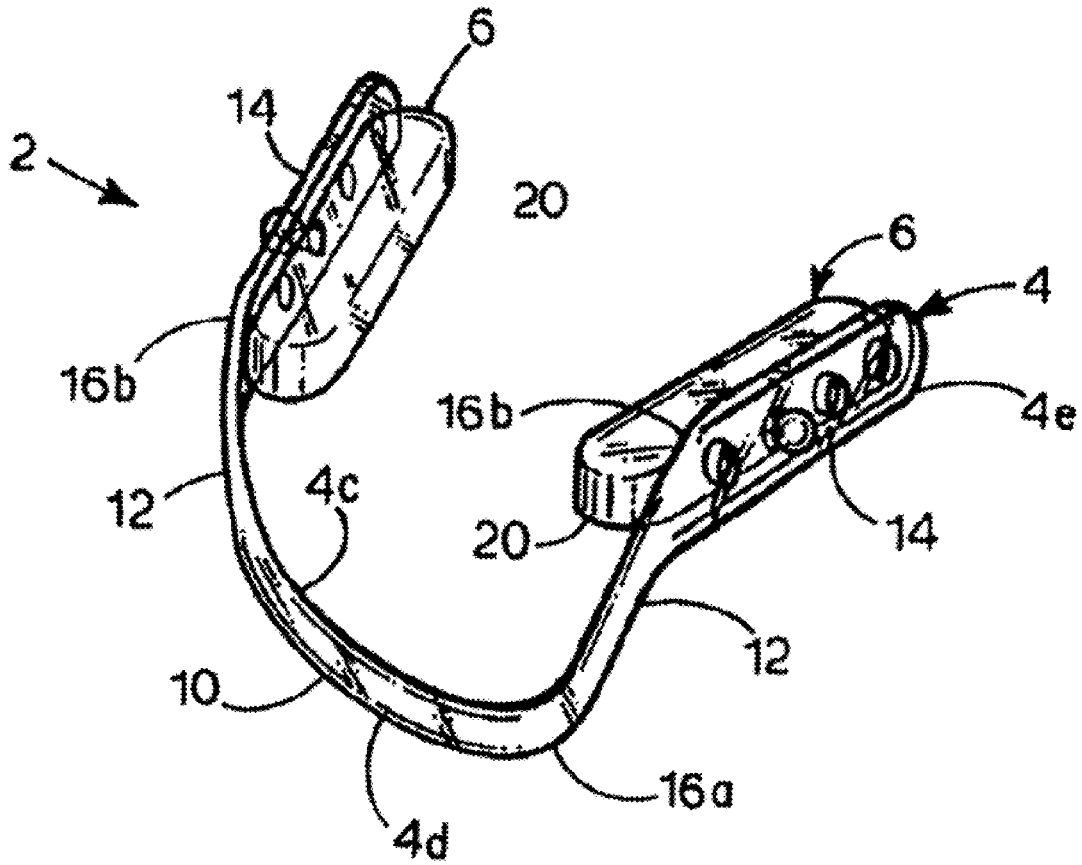

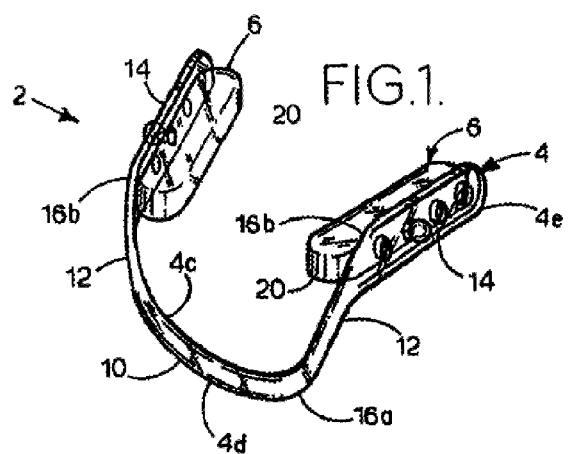
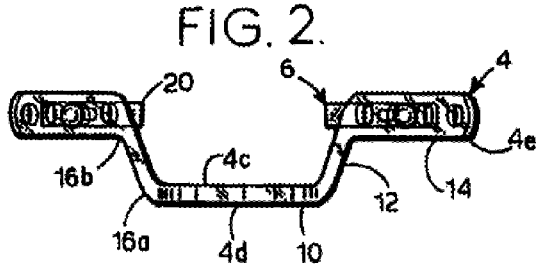
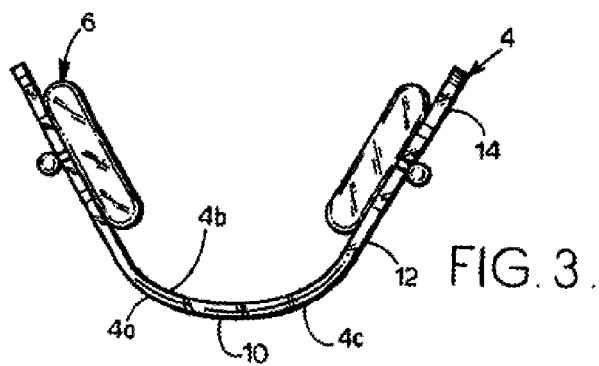

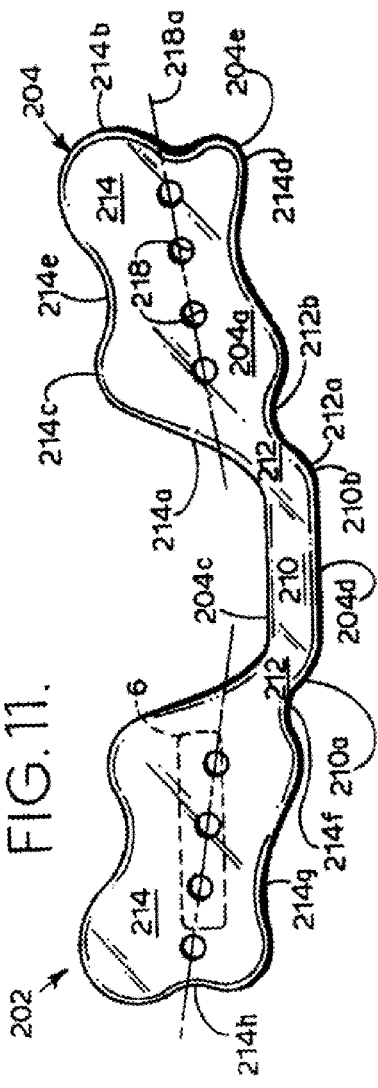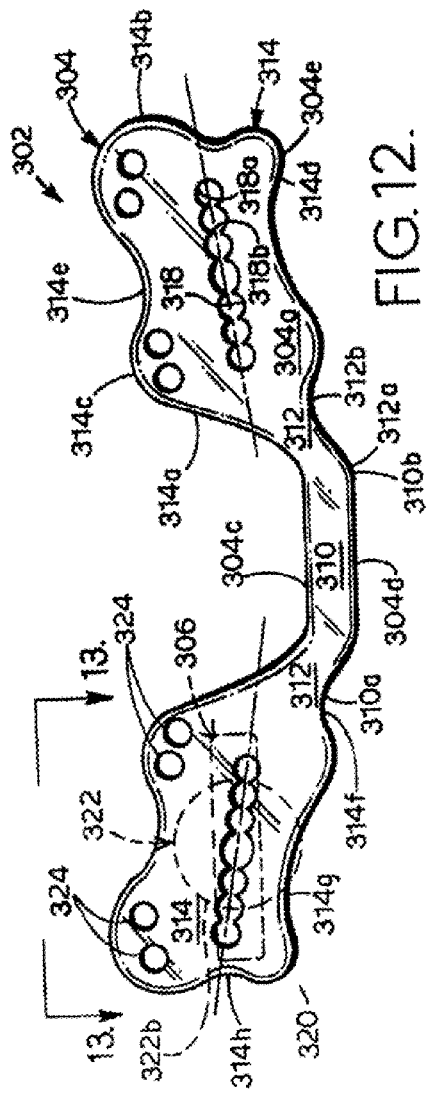

What is claimed and desired to be secured by Letters Patent is as follows:

1. A kinesiologic mouthpiece, which comprises:
   (a) a strap assembly;
   (b) a pair of bitepad assemblies each including a bitepad with:
      (1) an inner core; and
      (2) an outer core;
      (3) an upper surface;
      (4) a lower surface;
      (5) a span; and
      (6) an interface between said upper and lower surfaces and said span;
   (c) a pair of bitepad mounting means for mounting said bitepad assembly to said strap assembly;
   (d) said inner core having inner, outer, front and rear edges;
   (e) a recess in said front edge and a recess in said rear edge; and
   (f) a plurality of openings extending through said inner core.

2. The mouthpiece, according to claim 1, wherein each said inner core includes:
   (a) a front portion;
   (b) a rear portion;
   (c) said inner core front portion being narrower than said bitepad back end; and
   (d) said inner core inner edges converging from rear to front towards said inner core outer edges respectively.

3. The mouthpiece, according to claim 2, wherein said outer edge of said outer core tapers inward along a distal portion thereof.

4. The mouthpiece, according to claim 2, wherein the corners between said inner, outer, front and rear edges are rounded.

5. The mouthpiece, according to claim 1, wherein said interfaces between said upper and lower surfaces and said span are rounded.

6. The mouthpiece, according to claim 1, wherein said span tapers inward along a distal end thereof.

7. A kinesiologic mouthpiece, which comprises:
   (a) a strap assembly;
   (b) a pair of bitepad assemblies each including a bitepad with:
      (1) an inner core; and
      (2) an outer core with an upper contact surface, a lower contact surface, an inner edge, an outer edge, a front edge, a rear edge, a front portion and a rear portion;
   (c) a pair of bitepad mounting means for mounting said bitepad assembly to said strap assembly;
   (d) said outer core including corners formed between said inner, outer, front and rear edges;
   (e) said outer core front portion being narrower than said rear portion; and
   (f) said outer core inner edges converging from front to back towards said outer core outer edges respectively.

* * * * *

UNITED STATES PATENT AND TRADEMARK OFFICE
CERTIFICATE OF CORRECTION

PATENT NO. : 6,152,138
APPLICATION NO. : 09/256004
DATED : November 28, 2000
INVENTOR(S) : Brown et al.

It is certified that error appears in the above-identified patent and that said Letters Patent is hereby corrected as shown below:

The title page, showing an illustrative figure, should be deleted and substitute therefor the attached title page.

Delete Drawing Sheets 1-6 and substitute therefor the Drawing sheets consisting of Figures 1-18 as shown on the attached pages.

Signed and Sealed this

Twentieth Day of January, 2009

JON W. DUDAS
*Director of the United States Patent and Trademark Office*

United States Patent [19]

Brown et al.

[11] Patent Number: 6,152,138
[45] Date of Patent: Nov. 28, 2000

[54] KINESIOLOGIC MOUTHPIECE AND METHOD

[76] Inventors: Thomas J. Brown, 1146 Guinevere; Thomas W. Brown, 1421 LaChateau, both of Liberty, Mo. 64068

[21] Appl. No.: 09/256,004

[22] Filed: Feb. 23, 1999

Related U.S. Application Data

[63] Continuation-in-part of application No. 08/695,390, Aug. 12, 1996, Pat. No. 5,873,365.

[51] Int. Cl.[7] .................................................. A61C 5/14
[52] U.S. Cl. ..................................... 128/859; 128/861
[58] Field of Search ................................. 128/846, 848, 128/859–862

[56] References Cited

U.S. PATENT DOCUMENTS

| | | | |
|---|---|---|---|
| 3,532,091 | 10/1970 | Lerman | 128/861 |
| 3,682,164 | 8/1972 | Miller | 128/861 |
| 4,063,552 | 12/1977 | Goisg | 128/859 |
| 5,339,832 | 8/1994 | Kittelsen | 128/862 |

Primary Examiner—Michael A. Brown
Attorney, Agent, or Firm—Shughart, Thomson, & Kilroy, P.C.

[57] ABSTRACT

A kinesiological mouthpiece includes a strap assembly with a bridge, a pair of extensions extending generally rearwardly and outwardly from the bridge and a pair of wings extending generally rearwardly from the extensions. The strap assembly is flexible for forming in a generally U-shaped use configuration. The wings are displaced at a different level from the bridge whereby the bridge can be positioned generally between the lower teeth and the lower lip with the wings approximately located on bite lines of the back teeth. A pair of bitepad assemblies are rotatably and longitudinally-adjustably mounted on the wings and each includes a bitepad with upper and lower contact surfaces for contacting by the back teeth. An occlusal support method includes the steps of providing a strap assembly, placing the strap assembly around the lower teeth, adjustably and rotatably mounting a pair of bitepad assemblies on the strap assembly, placing the bitepad assemblies between the back teeth and relieving tension on the temporomandibular joint.

7 Claims, 8 Drawing Sheets